United States Patent [19]

Nagasawa et al.

[11] Patent Number: 4,868,114
[45] Date of Patent: Sep. 19, 1989

[54] METHOD FOR ELEVATING GLUTATHIONE LEVELS

[75] Inventors: Herbert T. Nagasawa, Richfield, Minn.; Jeanette C. Roberts, Sante Fe, N. Mex.

[73] Assignee: Regents of the University of Minnesota, Minneapolis, Minn.

[21] Appl. No.: 296,863

[22] Filed: Jan. 13, 1989

Related U.S. Application Data

[63] Continuation of Ser. No. 81,844, Aug. 5, 1987, abandoned.

[51] Int. Cl.[4] .............................................. C12D 13/12
[52] U.S. Cl. .................................... 435/112; 435/231; 435/234; 514/23; 514/365
[58] Field of Search ................. 514/23, 365; 435/113, 435/231, 234, 112

[56] References Cited

U.S. PATENT DOCUMENTS

| | | | |
|---|---|---|---|
| 3,950,529 | 4/1976 | Fischer et al. | 514/400 |
| 4,017,608 | 4/1977 | Gordon | 514/25 |
| 4,335,210 | 6/1982 | Meister et al. | 435/113 |

OTHER PUBLICATIONS

C. D. Klaasen et al., *Fundamental and Applied Toxicology*, 5, 805 (1985).
H. T. Nagasawa et al., *J. Med. Chem.*, 27, 591 (1984).
J. M. Williamson et al., *PNAS USA*, 79, 6246 (1982).
J. M. Williamson et al., *PNAS USA*, 78, 936 (1981).
R. Garnier et al., *J. Toxicol.: Clin. Toxicol.*, 19, 289 (1982).
H. T. Nagasawa et al., *J. Med. Chem.*, 25, 489 (1982).
L. F. Prescott et al., *Brit Med. J.*, 2, 1097 (1979).
B. H. Lautenberg et al., *J. Clin. Invest.*, 71, 980 (1983).
G. B. Corcoran et al., *J. Pharmacol. Exper. Ther.*, 232, 864 (1985).
O. W. Griffith et al., *J. Biol. Chem.*, 254, 7558 (1979).
V. F. Korber et al., *Z. Klin. Chem. and Klin. Biochem.*, 6, 289 (1968).
G. Weitzel et al., *Hoppe-Seyler's Z. Physiol. Chem.*, 315, 236 (1959).
R. Bognar et al., *Z. Liebigs Ann. Chem.*, 738, 68 (1970).

*Primary Examiner*—William R. Dixon, Jr.
*Assistant Examiner*—Karl Group
*Attorney, Agent, or Firm*—Merchant, Gould, Smith, Edell, Welter & Schmidt

[57] ABSTRACT

A method comprising stimulating the biosynthesis of glutathione in mammalian cells by contacting the cells with an effective amount of a compound of the formula:

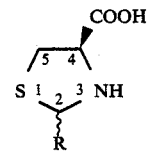

wherein R is a $(CHOH)_nCH_2OH$ and wherein n is 1-5, preferably R is derived from a D-aldose monosaccharide.

13 Claims, 1 Drawing Sheet

METHOD FOR ELEVATING GLUTATHIONE LEVELS

This invention was made with the support of Grant 5-T32-GM07994, awarded by the United States Public Health Service. The Government has certain rights in the invention.

This is a continuation of application Ser. No. 81,844 abandon, filed Aug. 5, 1987, which was abandoned upon the filing hereof.

BACKGROUND OF THE INVENTION

A wide range of xenobiotic substances, including many useful drugs, are metabolized by hepatic cytochrome P-450 enzymes to toxic electrophilic species, which can cause liver necrosis and lead to death. Such drugs include many antibiotics, antiinflammatory drugs, analgesics, halogenated hydrocarbons and antitumor drugs. The protective mechanisms of mammalian cells employ the co-enzyme, glutathione (GSH), which is important in maintaining the structural integrity of cell and organelle membranes and in the synthesis of microtubules and macromolecules. See C. D. Klassen et al., *Fundamental and Applied Toxicology*, 5, 806 (1985). Stimulation of GSH synthesis in rat renal epithelial cells and stomach cells has been found to protect the cells from the toxic effects of cyclophosphamide and serotonin, respectively. Conversely, inhibition of glutathione synthesis has been found to have the following effects: (a) decreased cell viability, (b) increased sensitivity of cells to the effects of irradiation, (c) increased sensitivity of tumor cells to peroxide cytolysis, (d) decreased synthesis of prostaglandin E and leukotriene C and (e) selective destruction of trypanosomes in mice.

It has been hypothesized that delivery of L-cysteine to mammalian cells would elevate GSH levels by supplying this biochemical GSH precursor to the cell. However, cysteine itself is toxic when administered to mammals, and is rapidly degraded.

In previous studies, it was shown that N-acetyl-L-cysteine, L-2-oxothiazolidine-4-carboxylate, as well as 2(R,S)-n-propyl-, 2(R,S)-n-pentyl and 2(R,S)-methyl-thiazolidine-4R-carboxylate can protect mice from hepatotoxic dosages of acetaminophen. See H. T. Nagasawa et al., *J. Med. Chem.*, 27, 591 (1984) and A. Meister et al., U.S. Pat. No. 4,335,210. L-2-Oxothiazolidine-4-carboxylate is converted to L-cysteine via the enzyme 5-oxo-L-prolinase. As depicted in FIG. 1, compounds of formula 1, e.g., wherein R=CH$_3$, function as prodrug forms of L-cysteine (2), liberating this sulfhydryl amino acid by nonenzymatic ring opening and hydrolysis. However, the dissociation to yield L-cysteine necessarily releases an equimolar amount of the aldehyde (3), RCHO. In prodrugs in which R is an aromatic or an alkyl residue, the potential for toxic effects is present.

Therefore, a need exists for cysteine prodrugs which are effective to raise cellular glutathione levels, e.g., which can act as hepatoprotective agents, while not releasing toxic aldehydes during intracellular degradation.

BRIEF DESCRIPTION OF THE INVENTION

Figure 1:
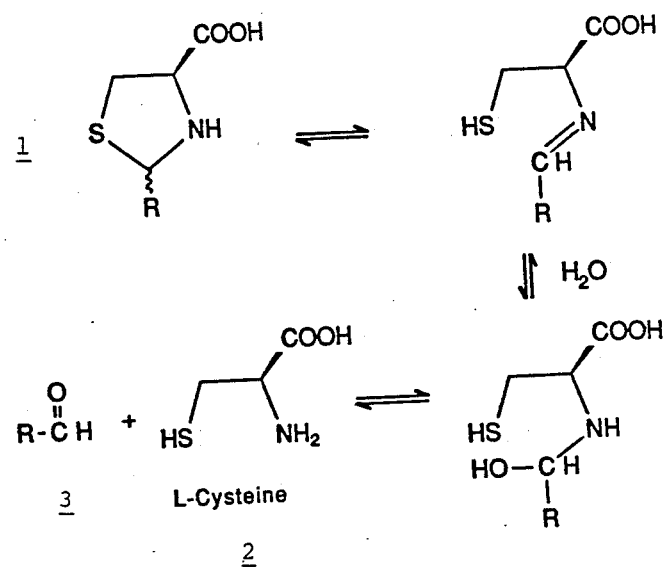
FIG. 1 schematically depicts the release of L-cysteine (2) from the heterocyclic prodrug (1).

The present invention is directed to a method comprising stimulating the biosynthesis of glutathione in mammalian cells by contacting the cells with an effective amount of a compound of the formula (1):

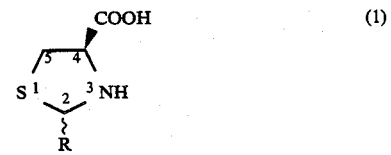

wherein R is a (CHOH)$_n$CH$_2$OH and wherein n is 1–5. Preferably, the present method employs compounds of formula (1), wherein R is derived from a D-aldose monosaccharide residue. Particularly preferred compounds of formula (1) are depicted in Table 1, below.

TABLE 1

Prodrugs of L-Cysteine

| Cpd No. | 1a | 1b | 1c | 1d | 1e | 1f | 1g | 1h |
|---|---|---|---|---|---|---|---|---|
| R = | —OH<br>—OH | HO—<br>—OH<br>—OH<br>—OH | HO—<br>HO—<br>—OH<br>—OH | —OH<br>—OH<br>—OH<br>—OH | —OH<br>HO—<br>—OH<br>—OH | —OH<br>HO—<br>HO—<br>—OH<br>—OH | —OH<br>HO—<br>—OH<br>—OH<br>—OH | —OH<br>HO—<br>HO—<br>—OH<br>—OH<br>—OH |

As depicted in FIG. 1, compounds of formula 1 act as "prodrug" forms of L-cysteine (2), liberating L-cysteine and a non-toxic aldehyde RCHO (3) when the prodrug is nonenzymatically degraded in vivo. L-cysteine then acts to elevate cellular GSH levels in the target tissue. The GSH co-enzyme in turn initiates protective mechanisms against reactive electrophilic species generated during the oxidative metabolism of cytotoxic species. For example, an acetaminophen overdose depletes hepatic glutathione, allowing damage to normal cellular constituents. Supplying L-cysteine, one of the amino acid precursor of glutathione, stimulates glutathione biosynthesis and may amplify the existing protective mechanism. Therefore, the present invention provides a method for the nonenzymatic delivery of L-cysteine to mammalian cells in vitro or in vivo via the in situ hydrolytic dissociation of a compound of formula 1.

The wedge-shaped bond at $C_4$ of formula 1 indicates that the COOH group is positioned above the plane of the heterocyclic ring atoms. The wavy bond at $C_2$ of the ring indicates that the R group may be either above or below this ring. However, separation of this mixture of stereoisomers of the compound of formula 1 into the 2R,4R or 2S,4R enantiomers can be accomplished by resolution techniques known to the art. Given the proposed mechanism of L-cysteine release, there is no reason to believe that the resolved compounds would not be at least as active as the parent 2RS,4R compound, and accordingly, the use of the resolved compounds is within the scope of the present method.

The present invention also includes the pharmaceutically acceptable carboxylate salts of the compound formula 1. For example, these can include the alkali metal and alkaline earth metal salts of the 4-carboxylic acid group. Also included are the amine carboxylate salts, such as those formed by reacting the carboxylic acid group of 1 with a basic amino acid such as arginine. The amino acid can be reacted with compound I in an alcoholic solvent in a 1:1 molar ratio, and the salt precipitated from the reaction mixture with ether, or isolated by lyophilization.

The RCH-moiety in the compound of formula 1 may be derived from D-aldoses other than those depicted in Table 1, including D-allose, D-erythrose, D-threose, D-talose, D-idose, D-altrose, and D-gulose.

DETAILED DESCRIPTION OF THE INVENTION

I. Synthesis

The cysteine prodrugs useful in the present method can be prepared by treating L-cysteine with an enantiomerically pure $C_3$–$C_6$ aldose monosaccharide in water, methanol, ethanol, aqueous methanol or aqueous ethanol at about 20°–80° C., preferably in the presence of pyridine under an inert atmosphere. After a sufficient reaction time, e.g., 0.5–2.0 hours at reflux, the reaction mixture is cooled and the precipitated solid product collected and dried.

II. Administration

The cysteine prodrugs useful in the present method are soluble or dispersable in aqueous systems. Useful aqueous solvent systems include physiological salt solutions intended for parenteral administration, including Ringer's Injection, Lactated Ringer's Injection, Dextrose and NaCl injection and the like. See *Remington's Pharmaceutical Sciences*, A. Osol, ed., Mack Pub. Co. (16th ed. 1980) at pages 1488–1496, the disclosure of which is incorporated by reference herein. The effective protective dosage of a given cysteine prodrug will vary widely, and will depend upon such factors as the age and physique of the patient, and the type and dose of the toxic compound sought to be counteracted and the organ affected. These dosages can be determined empirically by the art worker using animal models such as those discussed hereinbelow. For example, a total dose of about 1.0–5.0 mmol/kg of the cysteine prodrugs listed on Table 1 is effective to counteract an $LD_{90}$ dosage of acetaminophen in the mouse model.

III. Biological Results

A. Stimulation of Glutathione (GSH) Biosynthesis in Vitro and Inhibition by Buthionine Sulfoximine Compounds 1a through 1h were incubated in vitro with rat hepatocytes and the GSH levels were measured after 4 hrs. The levels are summarized in Table 2, below.

TABLE 2

Increased Glutathione [GSH] Content of Rat Hepatocytes after Incubation with L-Cysteine Prodrugs

| Cysteine Prodrug | Conc. (mM) | [GSH] ± SE (nmol/$10^6$ cells) | [GSH] Rel. to Controls |
|---|---|---|---|
| None (Control) | — | 35.4 ± 0.78 | 1.0 |
| GlcCys (1g) | 1.0 | 75.2 ± 2.15 | 2.1 |
| RibCys (1d) | 1.0 | 61.2 ± 1.52 | 1.7 |
| XylCys (1e) | 1.0 | 58.3 ± 0.99 | 1.6 |
| GalCys (1f) | 1.0 | 58.0 ± 2.00 | 1.6 |
| ManCys (1h) | 1.0 | 57.8 ± 0.87 | 1.6 |
| GlycCys (1a) | 1.0 | 46.1 ± 1.10 | 1.3 |
| LyxCys (1c) | 1.0 | 45.9 ± 1.95 | 1.3 |
| AraCys (1b) | 1.0 | 42.9 ± 2.17 | 1.2 |
| N—Acetyl-L-cysteine (NAC) | 2.5 | 45.8 ± 1.27 | 1.3 |

As can be seen from Table 2, all eight prodrugs elevated GSH levels 1.2- to 2.1-fold relative to controls in these hepatocytes. GlcCys (1 g) was the most effective compound in this series, elevating GSH levels to over twice those measured for the controls. N-Acetyl-L-cysteine (NAC), the drug presently used for the clinical treatment of acetaminophen overdoses, also raised GSH levels by 30% in this system, but required 2.5 times the concentration of the thiazolidine prodrugs for comparable elevation. (See L. F. Prescott et al., *Brit. Med. J.*, 2, 1097 (1979); B. J. Lautenburg et al., *J. Clin. Invest.*, 71, 980 (1983) and G. B. Corcoran et al., *J. Pharmacol. Exp. Ther.*, 232, 864 (1985)).

That GSH biosynthesis was stimulated by liberation of its biochemical precursor, L-cysteine, from the prodrugs, was indicated by experiments conducted in the presence of 0.20 mM buthionine sulfoxime (BSO). O. W. Griffith et al., *J. Biol. Chem.*, 254, 7558 (1979), have demonstrated that BSO is a specific inhibitor of *gamma*-glutamyl cysteine synthetase, the enzyme responsible for catalyzing the first step in GSH biosynthesis. The data summarized on Table 3, below, demonstrate that GSH levels were decreased by this inhibitor even in the presence of the prodrugs, thus providing evidence that the increased levels of GSH observed (Table 2) were indeed due to *de novo* GSH biosynthesis from the L-cysteine provided by the thiazolidine prodrugs.

TABLE 3

Inhibitory Effect of Buthionine Sulfoxime (BSO) on GSH Elevation Elicited by L-Cysteine Prodrugs in Rat Hepatocytes

| Prodrug (1.0 mM) | BSO (0.2 mM) | [GSH] ± SE (nmol/$10^6$ cells) | [GSH] Rel. to Controls |
|---|---|---|---|
| None (Control) | — | 35.4 ± 0.78 | 1.0 |
| None | + | 18.4 ± 2.08 | 0.5 |
| GlcCys (1g) | + | 25.4 ± 0.99 | 0.7 |
| RibCys (1d) | + | 16.2 ± 3.60 | 0.5 |
| XylCys (1e) | + | 22.6 ± 1.84 | 0.8 |
| GalCys (1f) | + | 23.2 ± 2.56 | 0.7 |

TABLE 3-continued

Inhibitory Effect of Buthionine Sulfoxime (BSO) on GSH Elevation Elicited by L-Cysteine Prodrugs in Rat Hepatocytes

| Prodrug (1.0 mM) | BSO (0.2 mM) | [GSH] ± SE (nmol/10⁶ cells) | [GSH] Rel. to Controls |
|---|---|---|---|
| ManCys (lh) | + | 18.9 ± 1.87 | 0.5 |
| GlycCys (la) | + | 18.3 ± 6.41 | 0.5 |
| LyxCys (lc) | + | 22.4 ± 1.98 | 0.6 |
| AraCys (lb) | + | 19.5 ± 3.75 | 0.6 |
| N—Acetyl-L-cysteine (NAC, 2.5 mM) | + | 25.5 ± 1.59 | 0.7 |

B. Protection Against Acetaminophen-Induced Hepatotoxicity in Mice

Compounds 1a through 1h were evaluated in a mouse model for their ability to protect against the hepatotoxic action of acetaminophen. The experimental protocol involved the administration of an $LD_{90}$ dose of acetaminophen, followed 30 min. later by the prodrug as potential protective agent. Toxicity was assessed based on overall survival data at 48 hrs, as well as on histological criteria of hepatocellular damage using the rating system of J. R. Mitchell et al., *J. Pharmacol. Exp. Ther.*, 187, 185 (1973). The results of this study are summarized on Table 4, below.

TABLE 4

Protection Against Acetaminophen-Induced Hepatotoxicity in Mice by Prodrugs of L—Cysteine

| Compounds[a] | Survival (48 hr) (Number) | Survival (48 hr) (%) | Number of Animals with necrosis 4+ | 3+ | 2+ | 1+ | 0 |
|---|---|---|---|---|---|---|---|
| Acetaminophen (A) | 2/12 | 17 | 11 | 0 | 1 | 0 | 0 |
| A + RibCys (ld) | 12/12 | 100 | 0 | 0 | 6 | 2 | 4 |
| A + XylCys (le) | 6/10 | 60 | 5 | 0 | 0 | 2 | 3 |
| A + GalCys (lf) | 6/10 | 60 | 4 | 0 | 2 | 3 | 1 |
| A + AraCys (lb) | 4/10 | 40 | 7 | 0 | 2 | 1 | 0 |
| A + ManCys (lh) | 4/10 | 40 | 6 | 0 | 1 | 0 | 3 |
| A + GlycCys (la) | 3/10 | 30 | 7 | 2 | 1 | 0 | 0 |
| A + LyxCys (lc) | 3/10 | 30 | 9 | 1 | 0 | 0 | 0 |
| A + GlcCys (lg) | 3/10 | 30 | 7 | 1 | 0 | 2 | 0 |
| A + N—Acetyl-L—Cysteine (NAC)[b] | 17/18 | 94 | 1 | 1 | 0 | 3 | 13 |

While all the prodrugs (1a through 1h) increased the number of survivors over untreated controls, the thiazolidine prodrug derived from the condensation of D-ribose and L-cysteine (RibCys, 1d) showed the greatest therapeutic promise, with 100% survival at 48 hr. RibCys also showed the best histopathological profile, with all sample liver specimens showing a necrosis rating of 2+ or below. Data for N-acetyl-L-cysteine (NAC) is supplied for comparison.

C. Discussion

The prodrugs derived from L-cysteine and the aldose monosaccharides were capable of being assimilated by hepatocytes. The increase in cellular levels of GSH elicited by these prodrugs (Table 2) and the inhibition of this effect by BSO (Table 3) in rat hepatocyte preparations suggest that the free L-cysteine liberated stimulated the biosynthesis of this co-enzyme. In vivo, all these prodrugs (1a through 1h) increased the survival of animals given $LD_{90}$ doses of acetaminophen (Table 4). Differences in absorption, distribution, excretion and metabolic disposition would be expected among the compounds represented by this series, and may account for the differential efficacies in vivo.

RibCys (1d) was the best hepatoprotective agent of the series, with 100% survival of the acetaminophen treated mice at 48 hr, the time at which the overall results were assessed. Histological evaluation of the extent of hepatic damage also verified the protection afforded by RibCys (1d). Its efficacy was comparable to other prodrugs of L-cysteine, viz., the 2-alkyl-substituted TCAs [H. T. Nagasawa et al., *J. Med. Chem.*, 27, 59 (1984)], 2-oxo-TCA [J. M. Williamson et al., *PNAS*, 79, 6246 (1982)] and NAC [E. Piperno et al., *Lancet*, 2, 738 (1976) and H. T. Nagasawa et al., *J. Med. Chem.*, 25, 489 (1982)]. All of these agents offer improved protection over that of L-cysteine itself and underscore the importance of the prodrug approach to drug design. It is clear that RibCys (1d) and the other compounds of the invention are able to deliver masked L-cysteine to the cell and liberate this sulfhydryl amino acid intracellularly, thereby stimulating the biosynthesis of GSH.

Thus, the present method for delivering L-cysteine to cells appears to be a viable means for augmenting the endogenous protective mechanism mediated by GSH, and it is believed that cytoprotection, particularly hepatoprotection, by these cysteine prodrugs may be generally applicable to a wide variety of xenobiotic substances that are inherently toxic electrophiles or which are metabolized to toxic, reactive electrophilic species.

The invention will be further described by reference to the following detailed examples, wherein melting points were determined on a Fisher-Johns melting point apparatus and are uncorrected. Optical activities were measured on a Perkin-Elmer 141 or Autopol III polarimeter, and IR spectra were obtained on a Perkin-Elmer 281 IR spectophotometer. Proton NMR spectra were obtained on a JOEL FX90 MHz or Nicolet 300 MHz spectrometer with tetramethylsilane (TMS) or 2,2-dimethyl-2-silapentane-5-sulfonate (DSS) as internal standard. The 300 MHz spectrometer was also used for carbon-13 NMR analyses with dimethylsulfoxide (DMSO) as solvent and internal standard. Unless otherwise indicated, Analtech silica gel HF plates were used for thin-layer chromatography (TLC) analyses, with visual detection of spots by iodine vapor, ninhydrin or Ellman's reagent. Elemental analyses were performed by Schwarzkopf Microanalytical Laboratory (Woodside, NY) or Galbraith Laboratories (Knoxville, TN) and are summarized on Table 5, hereinbelow. Chemicals were purchased from the following commercial vendors: Glyc, Ara, Rib, Lyx, Xyl, Gal, Man, all of D-configuration, and L-cysteine, Sigma Chemical Company (St. Louis, MO); acetaminophen, Aldrich Chemical Company (Milwaukee, WI); D-Glc; Mallinckrodt Chemical Company (St. Louis, MO); $CdCO_3$, Fluka Chemical Corporation (Hauppauge, NY); and [1-$^{13}$C]-D-Glc, KOR Isotopes (Cambridge MA).

Male Swiss-Webster mice were purchased from Biolab (St. Paul, MN). All animal studies were performed in adherence with guidelines established in the "Guide for the Care and Use of Laboratory Animals" published by the U.S. Department of Health and Human Resources (NIH Publication 85-23, revised, 1985). Animals were housed in facilities accredited by the American Association for the Accreditation of Laboratory Animal Care (AAALAC), and the research protocol was approved by the Animal Study Subcommittee of the Minneapolis VA Medical Center.

EXAMPLE I

2(R,S)-D-glycero-1',2'-Dihydroxyethylthiazolidine-4(R)carboxylic Acid (GlycCys, 1a)

This compound was prepared by the procedure of F. Korber et al., Z. Clin. Chem. Clin. Biochem., 6, 289 (1968), the disclosure of which is incorporated by reference herein, with the following modifications. The reaction was run under a nitrogen ($N_2$) atmosphere to reduce the possibility of oxidation of L-cysteine in aqueous medium. The resulting precipitate was collected and dried in vacuo overnight to give 0.47 g (40.5% yield) of pale yellow crystalline product, mp 126°–129° C. dec; $[\alpha]_D^{25} -130.6°$ (c=1.00, $H_2O$); IR (KBr) $\nu$3280 (br, OH, COO−), 1630 cm$^{-1}$ (COO−).

EXAMPLE II

2(R,S)-D-arabino-1',2',3',4'-Tetrahydroxybutylthiazolidine-4(R)-carboxylic Acid (AraCys, 1b)

This compound was synthesized using arabinose (Ara) in methanol (MeOH) by the method of G. Weitzel et al., Hoppe-Seyler's Z. Physiol. Chem., 315, 236 (1959), the disclosure of which is incorporated by reference herein. The solids were collected and dried in vacuo overnight to give 1.10 g (86.6% yield) of white crystalline product, mp 163°–165° C. dec. $[\alpha]_D^{25} -128.8°$ (c=1.04, $H_2O$); IR (KBr) $\nu$3460 (NH), 3255 (br, OH, COO−), 1625 cm$^{-1}$ (COO−).

EXAMPLE III

2(R,S)-D-lyxo-1',2',3',4'-Tetrahydroxybutylthiazolidine-4(R)-carboxylic Acid (LyxCys, 1c).

The procedure used for the synthesis of 1b was followed on a 20 mmol-scale using lyxose (Lyx) in 150 ml MeOH to give 4.16 g (82.2% yield) of 1c as a color less solid, mp 172°–175° C. dec. $[\alpha]_D^{25} -98.9°$ (c=1.00, $H_2O$); IR (KBr) $\nu$3245 (br, OH, COO−), 1610 cm$^{-1}$ (COO−).

EXAMPLE IV

2(R,S)-D-ribo-1',2',3',4'-Tetrahydroxybutylthiazolidine-4(R)-carboxylic Acid RIbCys, 1d).

This compound was synthesized using ribose (Rib) as described by R. Bognar et al., Z. Liebigs Ann. Chem., 738, 68 (1970), the disclosure of which is incorporated by reference herein. The product was collected to give 4.71 g (92.2% yield) of pale yellow material, mp 149°–151° C. dec. $[\alpha]_D^{25} -103.1°$ (c=0.52, $H_2O$); IR (KBr) $\nu$3220 (br, OH, COO−), 1610 cm$^{-1}$ (COO−).

EXAMPLE V

2(R,S)-D-xylo-1',2',3',4'-Tetrahydroxybutylthiazolidine-4(R)-carboxylic Acid (XylCys, 1e)

The procedure used for the synthesis of 1b was employed using xylose (Xyl) to give 0.95 g (74.8% yield) of colorless product, 1e, mp 119°–123° C. dec. $[\alpha]_D^{25} -97.8°$ (c=1.01, $H_2O$); IR (KBr) $\nu$, 3260 (br, OH, COO−), 1640 cm$^{-1}$ (COO−).

EXAMPLE VI

2(R,S)-D-galacto-1',2',3',4',5'-Pentahydroxypentyl-thiazolidine-4(R)-carboxylic Acid (GalCys, 1f)

The synthetic procedure for 1b was followed on 20 mmolscale using galactose (Gal) in 340 ml MeOH to give 4.38 g (93.5% yield) of 1f as a colorless product, mp 148° C. dec. $[\alpha]_D^{25} -66.9°$ (c=0.49, $H_2O$); IR (KBr) $\nu$3440 (NH), 3260 (br, OH, COO−), 1630 cm$^{-1}$ (COO−).

EXAMPLE VII

2(R,S)-D-gluco-1',2',3',4',5'-Pentahydroxypentyl-thiazolidine-4(R)-carboxylic Acid (GlcCys, 1g)

The procedure for the synthesis of 1b was followed using glucose (Glc) to give 1.12 g (78.9% yield) of 1g, mp 165° C. dec. $[\alpha]_D^{25} -89.7°$ (c=0.49, $H_2O$); IR (KBr) $\nu$3340 (br, OH, COO−), 1610 cm$^{-1}$ (COO−); $^{13}$C-NMR (DMSO) $\delta$36.46, 37.01 (C-5), 63.46, 63.57 (C-5'), 70.18, 71.76 (C-2), 64.39, 65.15, 70.64, 70.71, 70.73, 71.11, 71.39, 72.33, 74.46, (C-1'-4'; C-4), 172.78, 174.67 (COOH).

EXAMPLE VIII

2(R,S)-[2-$^{13}$C]-D-gluco-1',2',3',4',5'-Pentahydroxypentylthiazolidine-4(R)-carboxylic Acid ($^{13}$C-GlcCys; $^{13}$C-1g)

[1-$^{13}$C]-D-Glucose (Glc) (0.090 g, 0.50 mmol) was dissolved in hot methanol (40 ml) and L-cysteine (0.67 g, 5.5 mmol) was added. After heating under reflux for 2 min, unlabeled D-Glc (0.90 g, 5.0 mmol) was added, folowed by pyridine (0.5 ml) 5 min later. Additional MeOH (20 ml) was added after 5 min to aid dissolution, and the solution was heated under reflux for 4 hr. White fluffy material began to accumulate after 1 hr.

After cooling to room temperature, this product was collected to give 1.17 g (75.0% yield) of product, mp 161°–164° C. dec; $^{13}$C-NMR (DMSO) $\delta$36.46, 37.01 (C-5), 63.46, 63.57 (C-5'), 70.18, 71.76 (enhanced C-2), 64.39, 65.15, 70.64, 70.71, 70.73, 71.11, 71.39, 72.33, 74.46 (C-1'4'; C-4), 172.78, 174.67 (COOH).

EXAMPLE IX

2(R,S)-D-manno-1',2',3',4',5'-Pentahydroxypentyl-thiazolidine-4(R)-carboxylic Acid (ManCys, 1h)

The procedure for the synthesis of 1b was followed using mannose (Man) to give 1.35 g (95.1% yield) of 1h as white product, mp 172°–176° C. dec. $[\alpha]_D^{25} -64.0°$ (c=0.49, $H_2O$); IR (KBr) $\nu$3340 (br, OH, COO−), 1615 cm$^{-1}$ (COO−).

The results of the elemental analyses of compounds 1a–h are summarized on Table 5, below.

TABLE 5

| Compound | Formula | Calculated C | Calculated H | Calculated N | Found C | Found H | Found N |
|---|---|---|---|---|---|---|---|
| 1a | $C_6H_{11}NO_4S$ | 37.30 | 5.74 | 7.25 | 37.31 | 5.74 | 7.22 |
| 1b | $C_8H_{15}NO_6S$ | 37.90 | 5.97 | 5.53 | 37.77 | 6.07 | 5.29 |
| 1c | $C_8H_{15}NO_6S$ | 37.94 | 5.97 | 5.53 | 37.73 | 6.08 | 5.47 |
| 1d | $C_8H_{15}NO_6S$ | 37.94 | 5.97 | 5.53 | 37.94 | 6.21 | 5.29 |
| 1e | $C_8H_{15}NO_6S \cdot 0.5 H_2O$ | 36.64 | 6.15 | 5.34 | 36.70 | 6.36 | 5.48 |
| 1f | $C_9H_{17}NO_7S \cdot 0.5$ | 36.98 | 6.21 | 4.79 | 36.98 | 6.45 | 4.86 |

TABLE 5-continued

| Com- | | Elemental Analyses | | | | | |
|---|---|---|---|---|---|---|---|
| | | Calculated | | | Found | | |
| pound | Formula | C | H | N | C | H | N |
| 1g | H₂O C₉H₁₇NO₇S | 38.16 | 6.05 | 4.94 | 38.00 | 6.29 | 5.15 |
| 1h | C₉H₁₇NO₇S | 38.16 | 6.05 | 4.94 | 38.01 | 6.16 | 4.99 |

Stimulation of Glutathione Biosynthesis in Isolated Rat Hepatocytes by L-Cysteine Prodrugs and Inhibition by Buthionine Sulfoximine (BSO)

Rat hepatocytes were isolated following the methods of P. O. Seglen, *Exper. Cell R.s.*, 74, 450 (1972). After final plating, the hepatocytes were maintained in culture for 24 hr prior to use. Only primary cultures were used throughout the studies. The hepatocytes were incubated with the cysteine prodrugs for a 4-hr period, and after removal of media by aspiration, the cells were rinsed with cold phosphate-buffered saline and deproteinized with 5% sulfosalicylic acid. Total GSH content (GSH+GSSG) was determined by a modification of the DTNB [5,5'-dithiobis(2-nitrobenzoic acid)] glutathione reductase recycling method of F. Tietze, *Anal. Biochem.*, 27, 502 (1969). The GSH concentration in the sample was quantified by determining the cycling rate (ΔOD at 412 nm/min) of the sample. For the inhibition studies with BSO, the cells were pre-exposed to BSO (0.20 mM) before treatment with the L-cysteine prodrugs.

Protection of Mice Against Acetaminophen-Induced Hepatotoxicity

The prodrugs of L-cysteine were examined for their ability to protect against acetaminophen-induced hepatotoxicity in mice essentially as described by H. T. Nagasawa et al., *J. Med. Chem.*, 25, 489 (1982). Male Swiss-Webster mice (19 to 31 g) were fasted overnight but given free access to water. An LD₉₀ dose of acetaminophen (750 mg/kg, 4.97 mmol/kg, ip) was then administered, followed 30 min later by a 2.45 mmole/kg ip dose of the L-cysteine prodrug. All injection solutions were freshly prepared in sterile water, except where solubility problems required the use of sterile 0.1N aqueous NaHCO₃ or a slurry of the prodrug in 2% aqueous carboxymethylcellulose (CMC). The animals were then given food and water ad libitum and were observed over a 48-hr period.

Representative sections from the central lobe of the liver were obtained from those animals found dead at 12, 24 and 48 hr. Survivors at 48 hr were sacrificed by cervical dislocation and the liver sections were similarly excised and sectioned. All specimens were fixed on 10% buffered formalin and in Form-a-Less (PMP, Inc., San Diego, CA) and stained with hematoxylin and eosin. The extent of hepatic necrosis was evaluated histologically by an investigator who had no knowledge of the experimental protocols or sample identity.

The invention has been described with reference to various specific and preferred embodiments and techniques. However, it should be understood that many variations and modifications may be made while remaining within the spirit and scope of the invention.

What is claimed is:

1. A method comprising stimulating the biosynthesis of glutathione in mammalian cells by contacting the cells with an effective amount of a compound of the formula:

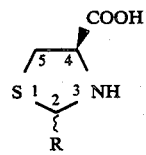

wherein R is a $(CHOH)_nCH_2OH$ and wherein n is 1–5, and the pharmaceutically acceptable salts thereof.

2. The method of claim 1 wherein the cells are liver cells.

3. The method of claim 1 wherein R is derived from a D-aldose monosaccharide.

4. The method of claim 3 wherein R is the $C_2$–$C_5$ residue of D-arabinose.

5. The method of claim 3 wherein R is the $C_2$–$C_5$ residue of D-lyxose.

6. The method of claim 3 wherein R is the $C_2$–$C_5$ residue of D-ribose.

7. The method of claim 3 wherein R is the $C_2$–$C_5$ residue of D-xylose.

8. The method of claim 3 wherein R is the $C_2$–$C_6$ residue due of D-galactose.

9. The method of claim 3 wherein R is the $C_2$–$C_6$ residue of D-glucose.

10. The method of claim 3 wherein R is the $C_2$–$C_6$ residue of D-mannose.

11. The method of claim 3 wherein R is the $C_2$–$C_3$ residue of D-glyceraldehyde.

12. The method of claim 1 wherein the compound is administered to a mammal parenterally in aqueous solution.

13. The method of claim 12 wherein the compound is administered intravenously.

* * * * *

UNITED STATES PATENT AND TRADEMARK OFFICE
CERTIFICATE OF CORRECTION

PATENT NO. : 4,868,114

DATED : September 19, 1989

INVENTOR(S) : H. T. Nagasawa, et al.

It is certified that error appears in the above-identified patent and that said Letters Patent is hereby corrected as shown below:

At column 5, after Table 4, insert

-- a   Dose of acetaminophen: 750 mg/kg (4.97 mmol/kg), ip; dose of prodrugs: 2.45 mmol/kg, ip. Protocol described in Section B, above.

b   Data from H. T. Nagasawa et al., J. Med. Chem., 25, 489 (1982); dose of NAC: 2.45 mmol/kg, ip.

--.

At column 9, line 14, "R.s." should read --Res.--.

Signed and Sealed this

Twenty-eighth Day of May, 1991

Attest:

HARRY F. MANBECK, JR.

Attesting Officer    Commissioner of Patents and Trademarks